US012636050B2

(12) United States Patent     (10) Patent No.: US 12,636,050 B2

Wallace et al.     (45) Date of Patent: May 26, 2026

(54) EXPANDIBLE-EXTENDIBLE INTRAMEDULLARY NAIL

(71) Applicant: IRF Medical LLC, Norristown, PA (US)

(72) Inventors: Zachary Wallace, Philadelphia, PA (US); Mark Hedgeland, Norristown, PA (US); Lauren Gray, Phoenixville, PA (US)

(73) Assignee: IRF Medical LLC

( * ) Notice: Subject to any disclaimer, the term of this patent is extended or adjusted under 35 U.S.C. 154(b) by 0 days.

(21) Appl. No.: 19/053,463

(22) Filed: Feb. 14, 2025

(65) Prior Publication Data

US 2025/0255652 A1    Aug. 14, 2025

Related U.S. Application Data

(60) Provisional application No. 63/553,150, filed on Feb. 14, 2024.

(51) Int. Cl.
    *A61B 17/72*       (2006.01)
    *A61B 17/74*       (2006.01)

(52) U.S. Cl.
    CPC ...... *A61B 17/7275* (2013.01); *A61B 17/7283* (2013.01); *A61B 17/744* (2013.01); *A61B 17/748* (2013.01)

(58) Field of Classification Search
    CPC ........................................... A61B 17/72–7291
    See application file for complete search history.

(56) References Cited

U.S. PATENT DOCUMENTS

| | | | |
|---|---|---|---|
| 4,204,531 A | 5/1980 | Aginsky | |
| 5,387,239 A | 2/1995 | Bianco et al. | |
| 9,827,025 B2 | 11/2017 | Jansen | |
| 2009/0216283 A1* | 8/2009 | Gradl | A61B 17/7233 |
| | | | 606/329 |
| 2010/0010490 A1* | 1/2010 | Brigido | A61B 17/1775 |
| | | | 606/62 |
| 2011/0230883 A1 | 9/2011 | Zahrly et al. | |
| 2013/0116694 A1 | 5/2013 | Zurschmede | |
| 2013/0325008 A1 | 12/2013 | Kuxhaus et al. | |
| 2014/0135769 A1 | 5/2014 | Ziran | |

(Continued)

FOREIGN PATENT DOCUMENTS

| | | |
|---|---|---|
| EP | 2131767 B1 | 11/2017 |
| JP | 5628675 B2 | 11/2014 |

*Primary Examiner* — Nicholas J Plionis

(74) *Attorney, Agent, or Firm* — Gearhart Law, LLC

(57) ABSTRACT

The expandible-extendible intramedullary nail includes a base section. An assembly component is connected to the base section. The assembly component has an inner assembly surface and helical assembly threads formed on the inner assembly surface. A distal rod is connected to the assembly component. A driving nut is connected to the distal rod and assembly component. The driving nut has an outer nut surface and helical nut threads formed on the outer nut surface. The driving nut is rotatable about the longitudinal central axis of the helical nut threads such that the rotation causes helical displacement of the helical nut threads relative to the helical assembly threads. This causes longitudinal displacement of the distal rod relative to the assembly component.

14 Claims, 7 Drawing Sheets

(56) References Cited

U.S. PATENT DOCUMENTS

2015/0038968 A1* 2/2015 Vega .................. A61B 17/7266
606/64
2018/0353227 A1 12/2018 Kuxhaus et al.
2019/0358046 A1* 11/2019 Ehmke ............... A61B 17/1775

* cited by examiner

FIG. 10

EXPANDIBLE-EXTENDIBLE INTRAMEDULLARY NAIL

CROSS-REFERENCE TO RELATED APPLICATIONS

This application is a U.S. Non-Provisional Utility Patent Application entitled, "EXPANDIBLE-EXTENDIBLE INTRAMEDULLARY NAIL" which claims priority to co-pending U.S. Provisional Patent Application No. 63/553,150, filed on Feb. 14, 2024 entitled, "EXPANDIBLE-EXTENDIBLE INTRAMEDULLARY NAIL" the contents of which are hereby fully incorporated by reference.

FIELD OF THE EMBODIMENTS

The field of the invention and its embodiments relates to devices that may be implanted in the bones of humans and, more specifically, to expandible-extendible intramedullary nails and methods for using the expandible-extendible intramedullary nails.

BACKGROUND OF THE EMBODIMENTS

Intramedullary nails may be implanted in the bones of humans. A purpose of such nails may be to increase the longitudinal strength of the implanted bone. An example of this is the implantation of an intramedullary nail in a leg. When the leg in which the intramedullary nail is implanted is stood on, the longitudinal force on the nail will normally increase and be compressive. This will occur, for example, when the human to whom the leg is a part stands up and bears weight on the leg containing the intramedullary nail.

If the intramedullary nail is implanted in a human who is not fully grown, the growth of the human will normally increase the desired length of the intramedullary nail. For example, if the intramedullary nail is implanted in the leg of a human child, the desired length of the nail will increase as the child grows and its leg becomes longer.

The increase in the length of the leg of the child will result in the intramedullary nail then implanted in the leg becoming too short for the leg having the increased length. If the intramedullary nail is not replaced in vivo or lengthened, then the nail will most likely interfere with the proper longitudinal growth of the leg.

Replacing the intramedullary nail has drawbacks because it will require additional surgery(s). Normally, the preferred option for making the length of the nail compatible with the increasing length of the leg in which the nail is implanted is to implant a nail the length of which may be lengthened to remain compatible with the leg that is becoming longer due to growth.

Intramedullary nails may include outer surfaces having threads for elongation or retraction of the nail. Such threads may irritate the adjoining tissue due to the sharp crest at the transverse outermost region of the threads.

Intramedullary nails may include mechanisms which enable changes to the overall length of the nail. Such mechanisms may contain components the outer surfaces of which define portions of the outer surface of the nail thereby giving the nail an uneven, irregular outer surface. These components may move relative to other components of the intramedullary nail. This may cause irritation of the tissue adjoining the components that move.

SUMMARY OF THE EMBODIMENTS

The present invention and its embodiments relate to expandible-extendible intramedullary nails and methods for using the expandible-extendible intramedullary nails.

The expandible-extendible intramedullary nail includes an elongate tubular base section. An elongate tubular assembly component is connected to the base section. The assembly component has an inner assembly surface and helical assembly threads formed on the inner assembly surface. The assembly component and helical assembly threads each have a longitudinal central axis. The longitudinal central axes of the assembly component and helical assembly threads coincide with one another.

An elongate tubular distal rod is connected to the assembly component. The distal rod has a longitudinal central axis that coincides with the longitudinal central axis of the assembly component.

An elongate tubular driving nut is connected to the distal rod and assembly component. The driving nut has an outer nut surface and helical nut threads formed on the outer nut surface. The helical nut threads and distal rod each have a longitudinal central axis. The longitudinal central axes of the helical nut threads and distal rod coincide with one another. The helical nut threads correspond to the helical assembly threads.

The driving nut is rotatable about the longitudinal central axis of the helical nut threads such that the rotation causes helical displacement of the helical nut threads relative to the helical assembly threads. This, in turn, causes longitudinal displacement of the distal rod relative to the assembly component.

The expandible-extendible intramedullary nail may be lengthened or shortened while in the body of the human. Thus, replacing the intramedullary nail is not necessary if the part of the human, such as a leg, in which the intramedullary nail is implanted changes its longitudinal dimension. In the event of such a change, the longitudinal dimension of the intramedullary nail may be changed in vivo to accommodate the change in the longitudinal dimension of the part of the human in which the intramedullary nail is implanted.

The expandible-extendible intramedullary nail has mechanisms which cause the change in the longitudinal dimension of the nail. These mechanisms are contained within the outer surface of the intramedullary nail thereby giving the nail a smooth, even outer contour. Consequently, movement of these mechanisms does not cause associated forces on the tissue that adjoins the outer surface thereby reducing or preventing entirely irritation of this tissue.

US 12,636,050 B2

Figures 4, 5, 6, 7:
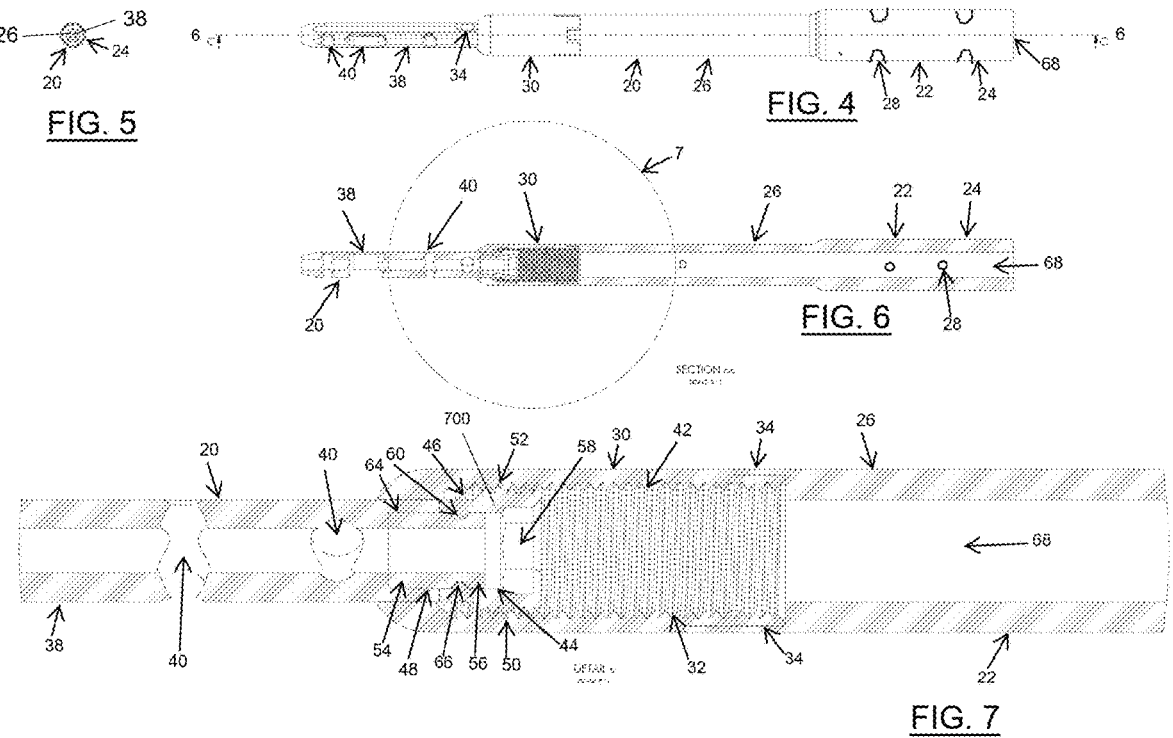
FIG. 4 depicts a plan view of the expandible-extendible intramedullary nail of FIG. 1 according to at least some embodiments described herein.
FIG. 5 depicts an end view of the expandible-extendible intramedullary nail of FIG. 4.
FIG. 6 depicts a cross sectional view of the expandible-extendible intramedullary nail of FIG. 4 in the plane indi-

3 cated by line 6-6 in FIG. 4 according to at least some embodiments described herein.

FIG. 7 depicts the portion of the expandible-extendible intramedullary nail of FIG. 6 enclosed by the circle 7, the portion of FIG. 6 enclosed by the circle 7 being enlarged in FIG. 7 according to at least some embodiments described herein.

Figures 1, 2, 3:
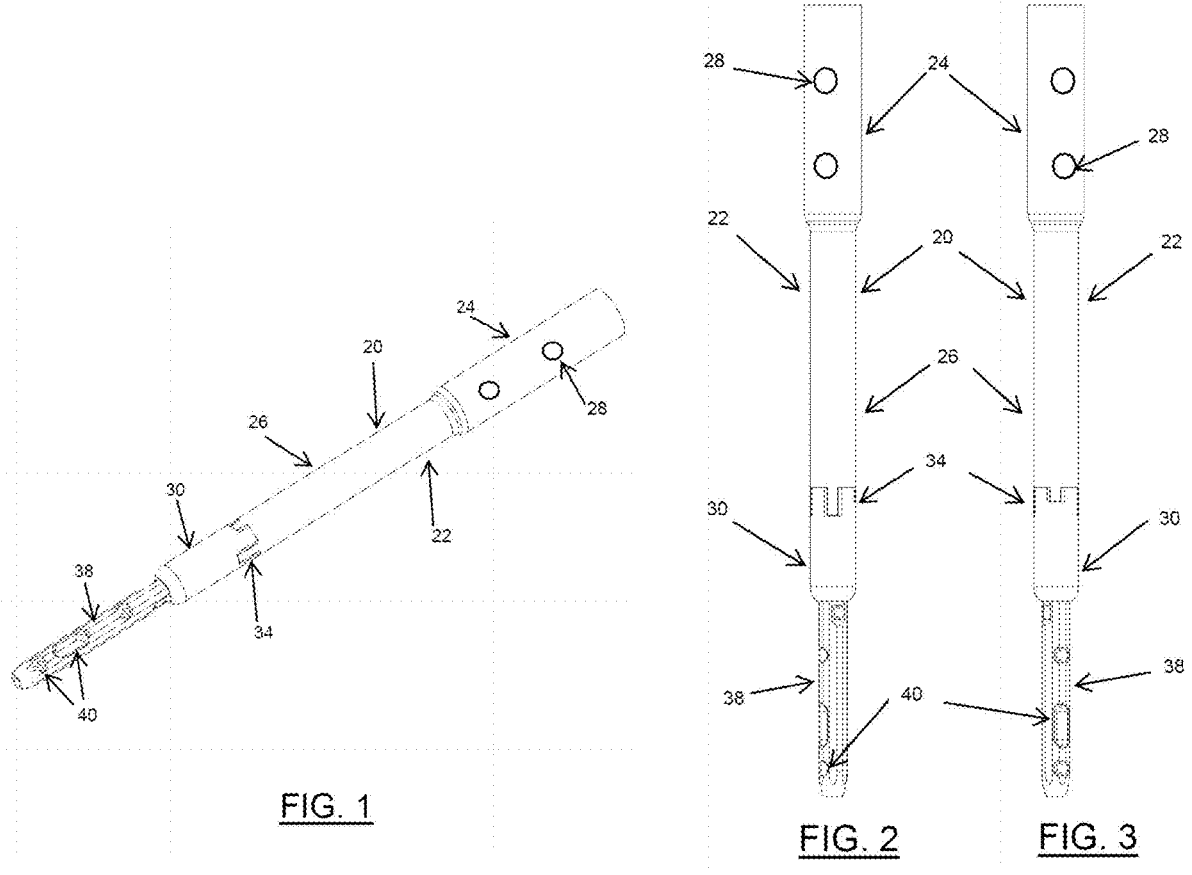
FIG. 1 depicts a perspective view of the expandible-extendible intramedullary nail according to at least some embodiments described herein.
FIG. 2 depicts a plan view of the expandible-extendible intramedullary nail of FIG. 1 showing the transverse holes extending through the distal rod according to at least some embodiments described herein.
FIG. 3 depicts a second plan view of the expandible-extendible intramedullary nail of FIG. 1 showing the nail rotated to illustrate the transverse holes of FIG. 2 at a different perspective according to at least some embodiments described herein.
Figures 8, 9:
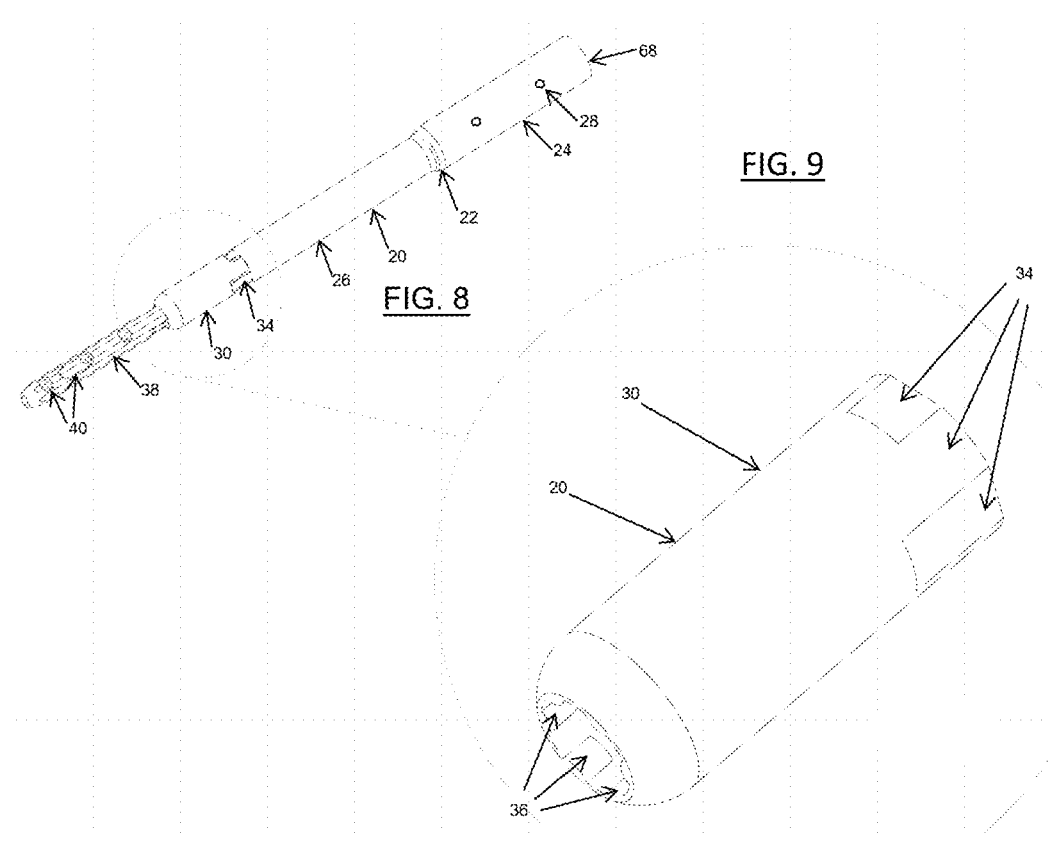

FIG. 8 depicts a perspective view of the expandible-extendible intramedullary nail of FIG. 1 according to at least some embodiments described herein.

FIG. 9 depicts an enlarged perspective view of the assembly component of the expandible-extendible intramedullary nail of FIG. 8 according to at least some embodiments described herein.

Figure 10:
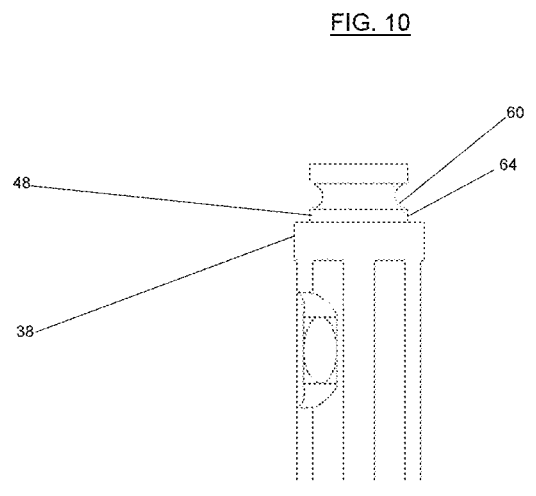

FIG. 10 depicts a side perspective view of the inner nut member of FIG. 7 with a transverse semi-circular recess forming a track on its outer surface according to at least some embodiments described herein.

Figure 11:
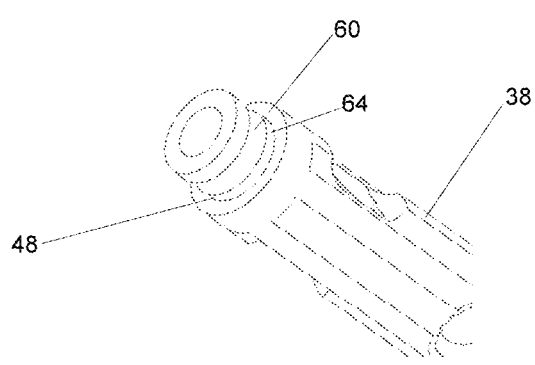

FIG. 11 depicts a perspective view of the inner nut member of FIG. 10 with a transverse semi-circular recess forming a track on its outer surface according to at least some embodiments described herein.

Figure 12:
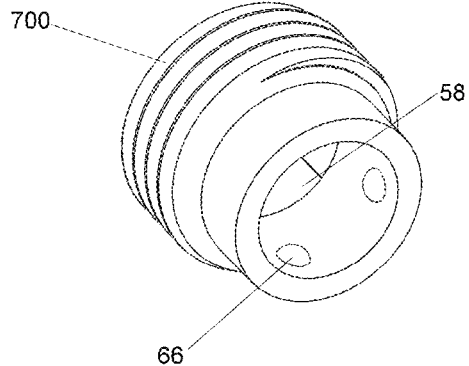

FIG. 12 depicts the locator nut of FIG. 7 with a partially threaded outer wall surface according to at least some embodiments described herein.

Figure 13:
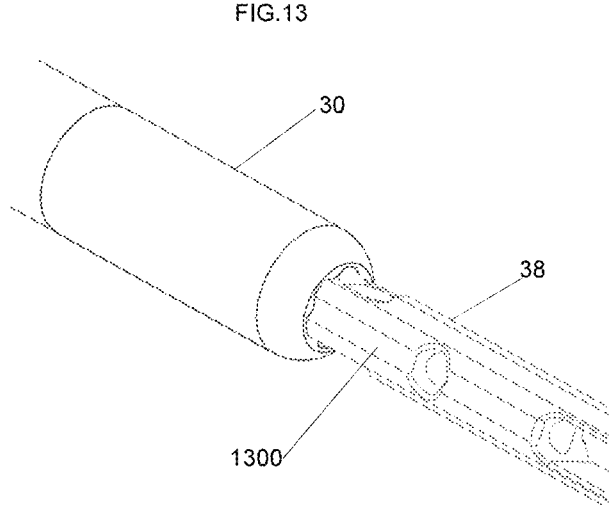

FIG. 13 depicts a perspective view of the assembly component 30 in communication with the distal rod of FIG. 8 with one or more anchor channels traversing the length of the distal rod according to at least some embodiments described herein.

DESCRIPTION OF THE PREFERRED
EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 ng" is intended to encompass 1 ng, 2 ng, 3 ng, 4 ng, 5 ng, 1-2 ng, 1-3 ng, 1-4 ng, 1-5 ng, 2-3 ng, 2-4 ng, 2-5 ng, 3-4 ng, 3-5 ng, and 4-5 ng.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

FIG. 1 shows the expandible-extendible intramedullary nail 20. The intramedullary nail 20 has an elongate base section 22 including an elongate tubular proximal rod 24. The base section 22 has an elongate tubular intermediate rod 26 having a proximal end that is connected to the distal end of the proximal rod 24. The proximal and intermediate rods 24, 26 each have respective longitudinal central axes that coincide with one another. The proximal and intermediate rods 24, 26 are formed of biocompatible materials since they will be lodged within the bone of a patient. Transverse holes 28 may extend through the proximal section 24.

FIG. 2 shows the expandible-extendible intramedullary nail 20. The intramedullary nail 20 has an elongate base section 22 including an elongate tubular proximal rod 24. The base section 22 has an elongate tubular intermediate rod 26 having a proximal end that is connected to the distal end of the proximal rod 24. The proximal and intermediate rods 24, 26 each have respective longitudinal central axes that coincide with one another. The proximal and intermediate rods 24, 26 are formed of biocompatible materials since they will be lodged within the bone of a patient. Transverse holes 28 may extend through the proximal section 24.

FIG. 3 shows the expandible-extendible intramedullary nail 20. The intramedullary nail 20 has an elongate base section 22 including an elongate tubular proximal rod 24. The base section 22 has an elongate tubular intermediate rod 26 having a proximal end that is connected to the distal end of the proximal rod 24. The proximal and intermediate rods 24, 26 each have respective longitudinal central axes that coincide with one another. The proximal and intermediate rods 24, 26 are formed of biocompatible materials since they will be lodged within the bone of a patient. Transverse holes 28 may extend through the proximal section 24.

FIG. 4 shows the expandible-extendible intramedullary nail 20. The intramedullary nail 20 has an elongate base section 22 including an elongate tubular proximal rod 24. The base section 22 has an elongate tubular intermediate rod 26 having a proximal end that is connected to the distal end of the proximal rod 24. The proximal and intermediate rods 24, 26 each have respective longitudinal central axes that coincide with one another. The proximal and intermediate rods 24, 26 are formed of biocompatible materials since they will be lodged within the bone of a patient. Transverse holes 28 may extend through the proximal section 24.

FIG. 5 illustrates a tapered orientation of the intramedullary nail 20. The elongate tubular proximal rod 24 has a diameter greater in size than the intermediate rod 26 and the distal rod 38.

FIG. 6 shows the expandible-extendible intramedullary nail 20. The intramedullary nail 20 has an elongate base section 22 including an elongate tubular proximal rod 24. The base section 22 has an elongate tubular intermediate rod 26 having a proximal end that is connected to the distal end of the proximal rod 24. The proximal and intermediate rods 24, 26 each have respective longitudinal central axes that coincide with one another. The proximal and intermediate rods 24, 26 are formed of biocompatible materials since they will be lodged within the bone of a patient. Transverse holes 28 may extend through the proximal section 24.

The intramedullary nail 20 has an elongate tubular assembly component 30. The assembly component 30 is formed of a biocompatible material since it will also be lodged within the bone of a patient.

FIG. 7 shows the portion of the expandible-extendible intramedullary nail 20 of FIG. 6 enclosed by the circle 7, the portion of FIG. 6 enclosed by the circle 7 being enlarged in FIG. 7. The distal end of the intermediate rod 26 is connected to the proximal end of the assembly component 30 as shown in FIG. 7. The intermediate rod 26 and assembly component 30 each have a longitudinal central axis. The longitudinal central axes of the intermediate rod 26 and assembly component 30 coincide with one another.

The wall thicknesses of the intermediate rod 26 and assembly component 30 are each reduced at circumferential sections of the connection between the intermediate rod 26 and assembly component as shown in FIG. 7. The reduced thickness distal section of the intermediate rod 26 is located within the reduced thickness proximal section of the assembly component 30 such that the outer surface of the reduced thickness distal section of the intermediate rod adjoins the inner assembly surface 32 of the reduced thickness proximal section of the assembly component as shown in FIG. 7. The reduced thickness distal and proximal sections constitute keying tabs 34 to facilitate the proper circumferential alignment of the intermediate rod 26 and assembly component 30 during manufacturing. The intermediate rod 26 and assembly component 30 are bonded together such as by welding, adhesives or other suitable technique.

FIG. 8 shows the expandible-extendible intramedullary nail 20. The intramedullary nail 20 has an elongate base section 22 including an elongate tubular proximal rod 24. The base section 22 has an elongate tubular intermediate rod 26 having a proximal end that is connected to the distal end of the proximal rod 24. The proximal and intermediate rods 24, 26 each have respective longitudinal central axes that coincide with one another. The proximal and intermediate rods 24, 26 are formed of biocompatible materials since they will be lodged within the bone of a patient. Transverse holes 28 may extend through the proximal section 24.

The distal rod 38 is connected to the assembly component 30. The distal rod 38 has a longitudinal central axis. The longitudinal central axes of the distal rod 38 and assembly component 30 coincide with one another. Transverse holes 40 extend through the distal rod 38 as shown in FIG. 1, FIG. 2, FIG. 3, FIG. 4, FIG. 6, FIG. 7, and FIG. 8.

FIG. 9 depicts an enlarged perspective view of the assembly component 30 of the expandible-extendible intramedullary nail 20 of FIG. 8. The distal end of the assembly component 30 has rotational locking tabs 36 that extend in a radially inward direction from the inner assembly surface 32 as shown in FIG. 9. The locking tabs 36 are integral with the assembly component 30. A recess corresponding to each locking tab 36 is formed on the inner surface of the distal rod 38 at its proximal end. The recesses extend in a radially inward direction relative to the inner surface of the distal rod 38. Each recess receives a corresponding locking tab 36 when the distal rod 38 is connected to the assembly component 30. The insertion of the locking tabs 36 into the recesses prevents the distal rod 38 from rotating when the distal rod is longitudinally displaced relative to the assembly component 30.

The assembly component 30 has helical assembly threads 42 formed on the inner assembly surface 32 as shown in FIGS. 6 and 7. The helical assembly threads 42 have a longitudinal central axis. The longitudinal central axes of the helical assembly threads 42 and assembly component 30 coincide with one another.

The intramedullary nail 20 has an elongate tubular driving nut 44 connected to the distal rod 38 and assembly component 30. The driving nut 44 includes cylindrical outer and inner nut members 46, 48 as shown in FIG. 7.

The outer nut member 46 has an outer nut surface 50 and helical nut threads 52 formed on the outer nut surface. The outer and inner nut members 46, 48, and distal rod 38 each have a longitudinal central axis. The longitudinal central axes of the outer and inner nut members 46, 48, and distal rod 38 coincide with one another. The helical nut threads 52 correspond to the helical assembly threads 42.

A distal section 54 of the inner nut member 48 is lodged within the distal rod 38 and assembly component 30 as shown in FIG. 7. A proximal section 56 of the inner nut member 48 is lodged within the outer nut member 46 and assembly component 30.

A locator nut 58 adjoins the proximal section 56 of the inner nut member 48 as shown in FIG. 7. The locator nut 58 is bonded to the outer nut member 46. The bonding may be provided by welding, adhesives or other suitable technique. The locator nut 58 has a transverse orientation relative to the longitudinal central axis of the inner nut member 48. The bonding of the locator nut 58 to the outer nut member 46 provides for rotation of the locator nut about its longitudinal central axis to cause associated rotation of the outer nut member about its longitudinal central axis.

The rotation of the outer nut member 46 about its longitudinal central axis causes helical displacement of the helical nut threads 52 relative to the helical assembly threads 42. This relative displacement causes longitudinal displacement of the outer nut member 46 relative to the assembly component 30. This longitudinal displacement causes longitudinal displacement of the driving nut 44 relative to the assembly component 30 which, in turn, causes longitudinal displacement of the distal rod 38 relative to the assembly component 30. Rotation of the driving nut 44 in a first direction causes displacement of the distal rod 38 in a distal direction away from the assembly component 30. Rotation of the driving nut 44 in a second direction causes retraction of the distal rod 38 into the assembly component 30. If the retraction of the distal rod 38 is sufficient, the distal rod may be retracted into the intermediate rod 26 and, possibly, the proximal rod 24.

The inner nut member 48 has a transverse semi-circular recess 60 on its outer surface 64. The semi-circular recess 60 has a longitudinal central axis that coincides with the longitudinal central axis of the inner nut member 48. Detents 66 extend, from an internal threaded washer 700, into the semi-circular recess 60. In other words, the semi-circular recess forms a track bordering the outer perimeter edge of the driving nut 44. This allows the driving nut 44 to spin freely during longitudinal displacement of the distal rod 38 relative to the assembly component 30.

The outer nut member 46 of the driving nut 44 is rotated about its longitudinal central axis by grasping the locator nut 58 and rotating it about its longitudinal central axis. The grasping of the locator nut 58 may be provided by inserting an elongate tool into the passage 68 (FIG. 4, FIG. 6, FIG. 7, FIG. 8) within the proximal rod 24 and intermediate rod 26 at the proximal end of the proximal rod. The tool is displaced in a distal direction until it reaches the locator nut 58. The locator nut 58 is then grasped by the tool and forcibly rotated in either the first or second directions depending upon whether the distal rod 38 is desired to be displaced away from the assembly component 30 in a distal direction, or retracted into the driving nut 44 and possibly the intermediate rod 26. Thus, in this embodiment, the distal rod 38, while having no threads, is longitudinally displaced relative to the assembly component 30.

The distal rod 38 may be longitudinally displaced relative to the assembly component 30 intra-operatively without removing the implant from the fractured bone. Intra-operatively refers to the longitudinal displacement of the distal rod 38 being possible with the intramedullary nail 20 being inside the bone and during a procedure. Also, the intramedullary nail 20 enables distal targeting with fluoroscopy through a targeting arm.

FIG. 10 and FIG. 11 illustrate the inner nut member 48 of FIG. 7 with a transverse semi-circular recess 60 forming a track on its outer surface 64. The inner nut member 48 is communicatively coupled to a first end of the non-rotatable distal rod 38 configured to partially traverse at least a portion of a threaded chamber of the assembly component 30 The inner nut member 48 is communicatively coupled to the locator nut 58 as detailed in FIG. 11.

FIG. 12 illustrates the locator nut 58 that is integrally formed within an internal threaded washer 700 with a partially threaded outer wall surface and with one or more detents 66 protruding from an inner wall surface. The internal threaded washer 700 is configured to be rotated so that the one or more detents 66 traverse at least a portion of the track of the semi-circular recess 60 (FIG. 10) of inner nut member 48 (FIG. 10). As the internal threaded washer 700 advances in a first extended orientation, it extends the distal rod 38, also referred to as a distal nail, and as the internal threaded washer 700 retracts, so does the distal rod 38. In other words, the rod 38 does not rotate which allows the hole alignments to stay the same. There are helical assembly threads 42 on an inner wall surface of the assembly component 30, also referred to as the proximal nail section, and one or more anchor channels 1300 traversing the length of the distal rod 38 to prevent distal rod 38 rotation as detailed in FIG. 13.

FIG. 13 illustrates the assembly component 30 in communication with the distal rod 38 of FIG. 8 with one or more anchor channels 1300 traversing the length of the distal rod 38 to prevent distal rod 38 rotation.

In some aspects, the techniques described herein relate to an expandible-extendible intramedullary nail including: an elongate tubular base section; an elongate tubular assembly component connected to the base section, the assembly component having an inner assembly surface and helical assembly threads formed on the inner assembly surface, the assembly component and helical assembly threads each having a longitudinal central axis, the longitudinal central axis of the assembly component and helical assembly threads coinciding with one another; an elongate tubular distal rod connected to the assembly component, the distal rod having a longitudinal central axis that coincides with the longitudinal central axis of the assembly component; and an elongate tubular driving nut connected to the distal rod and assembly component, the driving nut having an outer nut surface and helical nut threads formed on the outer nut surface, the helical nut threads and distal rod each having a longitudinal central axis, the longitudinal central axis of the helical nut threads and distal rod coinciding with one another, the helical nut threads corresponding to the helical assembly threads, the driving nut being rotatable about the longitudinal central axis of the helical nut threads such that the rotation causes helical displacement of the helical nut threads relative to the helical assembly threads which, in turn, causes longitudinal displacement of the distal rod relative to the assembly component.

In some aspects, the techniques described herein relate to an expandible-extendible intramedullary nail wherein a distal section of the driving nut is lodged within the distal rod, a proximal section of the driving nut is lodged within the assembly component, the driving nut having a circular recess on the outer nut surface into which one or more detents extend to allow the driving nut to spin freely during the longitudinal displacement of the distal rod relative to the assembly component.

In some aspects, the techniques described herein relate to an expandible-extendible intramedullary nail and further including a locator nut connected to the proximal section of the driving nut, the locator nut having a transverse orientation relative to the longitudinal central axis of the helical nut threads.

In some aspects, the techniques described herein relate to an expandible-extendible intramedullary nail and further including one or more transverse holes through the distal rod.

In some aspects, the techniques described herein relate to an expandible-extendible intramedullary nail and further including one or more transverse holes through the base section at a location proximal to the assembly component.

In some aspects, the techniques described herein relate to a method for operating an expandible-extendible intramedullary nail having a an elongate tubular base section, the intramedullary nail having an elongate tubular assembly component connected to the base section, the assembly component having an inner assembly surface and helical assembly threads formed on the inner assembly surface, the assembly component and helical assembly threads each having a longitudinal central axis, the longitudinal central axis of the assembly component and helical assembly threads coinciding with one another, the intramedullary nail having an elongate tubular distal rod connected to the assembly component, the distal rod having a longitudinal central axis that coincides with the longitudinal central axis of the assembly component, and the intramedullary nail having an elongate tubular driving nut connected to the distal rod and assembly component, the driving nut having an outer nut surface and helical nut threads formed on the outer nut surface, the helical nut threads and distal rod each having a longitudinal central axis, the longitudinal central axis of the helical nut threads and distal rod coinciding with one another, the helical nut threads corresponding to the helical assembly threads, the driving nut being rotatable about the longitudinal central axis of the helical nut threads, the method including rotating the driving nut about the longitudinal central axis of the helical nut threads, the rotation of the driving nut causing helical displacement of the helical nut threads relative to the helical assembly threads, the helical displacement of the helical nut threads relative to the helical assembly threads causing longitudinal displacement of the distal rod relative to the assembly component.

In some aspects, the techniques described herein relate to a method wherein the intramedullary nail further includes a locator nut connected to a proximal section of the driving nut, the locator nut having a transverse orientation relative to the longitudinal central axis of the helical nut threads, the method further including grasping the locator nut and rotating the locator nut about the longitudinal central axis of the helical nut threads, the rotation of the locator nut causing the rotation of the driving nut.

In some aspects, the techniques described herein relate to an intramedullary nail, including: a shaft with a bore traversing a length of the shaft; an internal wall surface of the bore of the shaft having a threaded portion; a threaded washer communicatively coupled to the threaded portion of the bore of the shaft; and a distal rod having an end of the distal rod communicatively coupled to the threaded washer.

In some aspects, the techniques described herein relate to an intramedullary nail, wherein the shaft having a tapered configuration.

In some aspects, the techniques described herein relate to an intramedullary nail, wherein the shaft having one or more openings.

In some aspects, the techniques described herein relate to an intramedullary nail, wherein the distal rod having one or more anchoring channels traversing a length of the distal rod.

In some aspects, the techniques described herein relate to an intramedullary nail, wherein the distal rod having one or more openings.

In some aspects, the techniques described herein relate to an intramedullary nail, wherein the distal rod has an inner nut member protruding therefrom, a recess forms a track around an outer wall surface of the inner nut member.

In some aspects, the techniques described herein relate to an intramedullary nail, wherein the threaded washer having one or more detents.

In some aspects, the techniques described herein relate to an intramedullary nail, wherein the one or more detents protrude from an inner wall surface of the threaded washer.

In some aspects, the techniques described herein relate to an intramedullary nail, wherein the distal rod is configured to be oriented in a retracted orientation when the threaded washer is rotated in a first direction.

In some aspects, the techniques described herein relate to an intramedullary nail, wherein the distal rod is configured to be slidably traversed within at least a portion of the bore of the shaft.

In some aspects, the techniques described herein relate to an intramedullary nail, wherein the distal rod is configured to be oriented in an extended orientation when the threaded washer is rotated in a second direction.

In some aspects, the techniques described herein relate to an intramedullary nail, wherein at least a portion of the distal rod is configured to be slidably traversed to protrude from the bore of the shaft.

In some aspects, the techniques described herein relate to an intramedullary nail, wherein the threaded washer having a locator nut configured to be engaged by a tool to implement a rotational force upon the threaded washer.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. An expandable-extendible intramedullary nail comprising:

an elongate tubular base section;

an elongate tubular assembly component connected to the base section, the assembly component having an inner assembly surface and helical assembly threads formed on the inner assembly surface, the assembly component and the helical assembly threads each having a longitudinal central axis, the longitudinal central axis of the assembly component and the helical assembly threads coinciding with one another;

an elongate tubular distal rod connected to the assembly component, the distal rod having a longitudinal central axis that coincides with the longitudinal central axis of the assembly component; and an elongate tubular driving nut connected to the distal rod and assembly component, the driving nut comprising:

an inner nut member with a proximal section having a semi-circular recess to form a track bordering an outer perimeter edge of the driving nut; and an internal threaded washer with helical nut threads located on an outer wall surface of the internal threaded washer, and one or more detents protruding from an inner wall surface of the internal threaded washer;

the driving nut being rotatable about the longitudinal central axis of the helical nut threads such that the rotation causes helical displacement of the helical nut threads relative to the helical assembly threads which, in turn, causes longitudinal displacement of the distal rod relative to the assembly component; and a distal section of the inner nut member of the driving nut is lodged within the distal rod, the proximal section of the inner nut member of the driving nut is lodged within the assembly component, the one or more detents of the internal threaded washer extends to traverse at least a portion of the track of the semi-circular recess of the inner nut member to allow the driving nut to spin freely during the longitudinal displacement of the distal rod relative to the assembly component.

2. The expandible-extendible intramedullary nail of claim 1 and further comprising a locator nut connected to the proximal section of the driving nut, the locator nut having a transverse orientation relative to the longitudinal central axis of the helical nut threads.

3. The expandible-extendible intramedullary nail of claim 1 and further comprising one or more transverse holes through the distal rod.

4. The expandible-extendible intramedullary nail of claim 1 and further comprising one or more transverse holes through the base section at a location proximal to the assembly component.

5. An intramedullary nail, comprising:

a shaft with a bore traversing a length of the shaft;

an internal wall surface of the bore of the shaft having a threaded portion;

an internal threaded washer communicatively coupled to the threaded portion of the bore of the shaft;

a distal rod having an end of the distal rod communicatively coupled to the internal threaded washer;

wherein the distal rod having one or more anchoring channels traversing a length of the distal rod;

a driving nut comprising:

an inner nut member with a proximal section having a semi-circular recess to form a track bordering an outer perimeter edge of the driving nut; and the internal threaded washer with helical nut threads located on an outer wall surface of the internal threaded washer, and one or more detents protruding from an inner wall surface of the internal threaded washer;

a distal section of the inner nut member of the driving nut is lodged within the distal rod, the proximal section of the inner nut member of the driving nut is lodged within the bore of the shaft, the one or more detents of the internal threaded washer extends to traverse at least a portion of the track of the semi-circular recess of the inner nut member to allow the driving nut to spin freely during longitudinal displacement of the distal rod relative to the shaft.

6. The intramedullary nail of claim 5, wherein the shaft having a tapered configuration.

7. The intramedullary nail of claim 5, wherein the shaft having one or more openings.

8. The intramedullary nail of claim 5, wherein the distal rod having one or more openings.

9. The intramedullary nail of claim 5, wherein the distal rod has the inner nut member protruding therefrom, a recess forms a track around an outer wall surface of the inner nut member.

10. The intramedullary nail of claim 5, wherein the distal rod is configured to be oriented in a retracted orientation when the threaded washer is rotated in a first direction.

11. The intramedullary nail of claim 10, wherein the distal rod is configured to be slidably traversed within at least a portion of the bore of the shaft.

12. The intramedullary nail of claim 5, wherein the distal rod is configured to be oriented in an extended orientation when the threaded washer is rotated in a second direction.

13. The intramedullary nail of claim 12, wherein at least a portion of the distal rod is configured to be slidably traversed to protrude from the bore of the shaft.

14. The intramedullary nail of claim 5, wherein the threaded washer having a locator nut configured to be engaged by a tool to implement a rotational force upon the threaded washer.

* * * * *